United States Patent [19]
Schroeder et al.

[11] Patent Number: 6,037,940
[45] Date of Patent: Mar. 14, 2000

[54] GRAPHICAL USER INTERFACE IN A MEDICAL PROTOCOL SYSTEM HAVING TIME DELAY RULES AND A PUBLISHER'S VIEW

[75] Inventors: Mark Steven Schroeder, Belmont; Annsheng C. Ting, Los Altos Hills; Chung-Jen Ho, San Jose; Kenneth L. Macrae, Atherton, all of Calif.

[73] Assignee: Araxsys, Inc., Redwood City, Calif.

[21] Appl. No.: 09/153,829

[22] Filed: Sep. 15, 1998

Related U.S. Application Data

[63] Continuation-in-part of application No. 08/546,212, Oct. 20, 1995, Pat. No. 5,850,221, and a continuation-in-part of application No. 08/546,213, Oct. 20, 1995, Pat. No. 5,826,237.

[51] Int. Cl.[7] .................................................. G06T 17/60
[52] U.S. Cl. ............................................ 345/348; 705/2
[58] Field of Search .................................... 345/326, 340, 345/348, 349, 352, 353, 354, 355, 356–357, 339, 327–328, 329–332, 333, 334–336; 705/2, 3, 100

[56] References Cited

U.S. PATENT DOCUMENTS

| | | | |
|---|---|---|---|
| 5,225,976 | 7/1993 | Tawil | 365/401 |
| 5,253,164 | 10/1993 | Holloway et al. | 364/406 |
| 5,404,292 | 4/1995 | Hendrickson | 364/413.02 |
| 5,583,758 | 12/1996 | McIlroy et al. | 395/202 |
| 5,660,176 | 8/1997 | Iliff | 128/630 |
| 5,826,237 | 10/1998 | Macrae et al. | 705/2 |
| 5,850,221 | 12/1998 | Macrae et al. | 345/348 |
| 5,874,964 | 2/1999 | Gille | 345/356 |
| 5,898,434 | 4/1999 | Small et al. | 345/348 |
| 5,918,208 | 6/1999 | Javitt | 705/2 |
| 5,946,659 | 8/1999 | Lanelit | 705/3 |
| 5,950,630 | 9/1999 | Portwood et al. | 128/897 |
| 5,953,704 | 9/1999 | McIlroy et al. | 705/2 |
| 5,960,403 | 9/1999 | Brown | 705/2 |

FOREIGN PATENT DOCUMENTS 0 457 000   11/1991   European Pat. Off. ........ G06F 15/42

OTHER PUBLICATIONS

Roger, et al., "Nursing Workload Management for a Patient Data Management System", 1992, IEEE, pp. 216–223.

Primary Examiner—Steven Sax
Attorney, Agent, or Firm—D'Alessandro & Ritchie

[57] ABSTRACT

A computer system is programmed to display a set of order triplet icons which are linked together to represent a medical treatment plan. Each of the order triplet icons represent a step within the medical treatment plan. Each link between two order triplet icons, such as a first order triplet icon and a second order triplet icon, represents a sequence between two steps within the medical treatment plan. Each sequence, as represented by a link, includes a rule which may be configured to have a time delay. When configured to have a time delay, the second order triplet icon is activated upon expiration of the time delay, forming a sequence from the first order triplet icon to the second order triplet icon. The computer system may also be programmed to display a medical treatment plan in process flow form, referred to as a publisher's view. The process flow shows the contents of a set of order triplet icons which may include at least one healthcare activity and at least one rule, and the relationship between the icons in the medical protocol.

37 Claims, 7 Drawing Sheets

6,037,940

GRAPHICAL USER INTERFACE IN A MEDICAL PROTOCOL SYSTEM HAVING TIME DELAY RULES AND A PUBLISHER'S VIEW

CROSS-REFERENCE TO RELATED APPLICATIONS

This application is a Continuation-In-Part application of co-pending application having application no. 08/546,212, entitled "APPARATUS AND METHOD FOR A GRAPHIC USER INTERFACE IN A MEDICAL PROTOCOL SYSTEM", filed on Oct. 20, 1995 U.S. Pat. No. 5,850,221 and a cip of U.S. patent application having application no. 08/546,213, entitled, "AN APPARATUS AND METHOD FOR MERGING MEDICAL PROTOCOLS", filed on Oct. 20, 1995 U.S. Pat. No. 5,826,237; hereinafter referred to as the "original patent applications," and hereby incorporated by reference as if fully set forth herein.

BACKGROUND OF THE INVENTION

1. Field of the Invention

The present invention relates to an improved medical protocol system having a graphical user interface which provides delayed activation of a step within the medical protocol and a publisher's view which shows the process flow of the medical protocol.

2. The Background Art

With the rising cost of healthcare, greater emphasis has been placed on providing healthcare services to patients at a consistent level of quality, while remaining cost-effective. Meeting these goals is a difficult endeavor because there are a variety of variables and factors that must be managed during treatment. For example, a medical protocol having more than one step may need to be implemented over a period of time, requiring the services of more than one medical provider, such as a day shift nurse and an evening shift nurse. Or the step performed may depend on the result of the previous step requiring the attention of a medical provider having a different skill set than the previous medical provider. Or the protocol may require steps that need to be performed by a team of medical providers, each having to perform different steps at different times. Or the medical protocol requires certain steps to occur at defined intervals, such as every eight hours or every day.

Accordingly a need exists for a graphical user interface-based medical protocol system that can provide delayed activation of a step defined within a medical protocol and that can generate a flow chart of the medical protocol so that the medical provider can ascertain the steps defined therein.

SUMMARY OF THE INVENTION

According to a first aspect of the present invention, a computer system is programmed to display a set of order triplet icons which are linked together to represent a medical treatment plan. Each of the order triplet icons represent a step within the medical treatment plan. Each link between two order triplet icons, such as a first order triplet icon and a second order triplet icon, represents a sequence between two steps within the medical treatment plan. Each sequence, as represented by a link, includes a rule which may be configured to have a time delay. When configured to have a time delay, the second order triplet icon is activated upon expiration of the time delay, forming a sequence from the first order triplet icon to the second order triplet icon.

According to a second aspect of the present invention, a computer system is programmed to display a medical treatment plan in process flow form, referred to as a publisher's view. The process flow shows the contents of a set of order triplet icons which may include at least one healthcare activity and at least one rule, and the relationship between the icons in the medical protocol.

DETAILED DESCRIPTION OF THE PREFERRED EMBODIMENTS

In the following description, a preferred embodiment of the invention is described with regard to preferred process steps and data structures. However, those skilled in the art would recognize, after perusal of this application, that embodiments of the invention may be implemented using a set of general purpose computers operating under program control, and that modification of a set of general purpose computers to implement the process steps and data structures described herein would not require undue invention.

In particular, a presently preferred embodiment of the present invention is described with reference to a medical protocol system having a Graphical user interface, such as those described in U.S. patent application having Ser. No. 08/546,212, entitled, "AN APPARATUS AND METHOD FOR A GRAPHIC USER INERFACE IN A MEDICAL PROTOCOL SYSTEM", filed on Oct. 20, 1995; and U.S. patent application having application no. 08/546,213, entitled, "AN APPARATUS AND METHOD FOR MERGING MEDICAL PROTOCOLS", filed on Oct. 20,1995; which are hereby incorporated by reference as if fully set forth herein.

Figure 1:
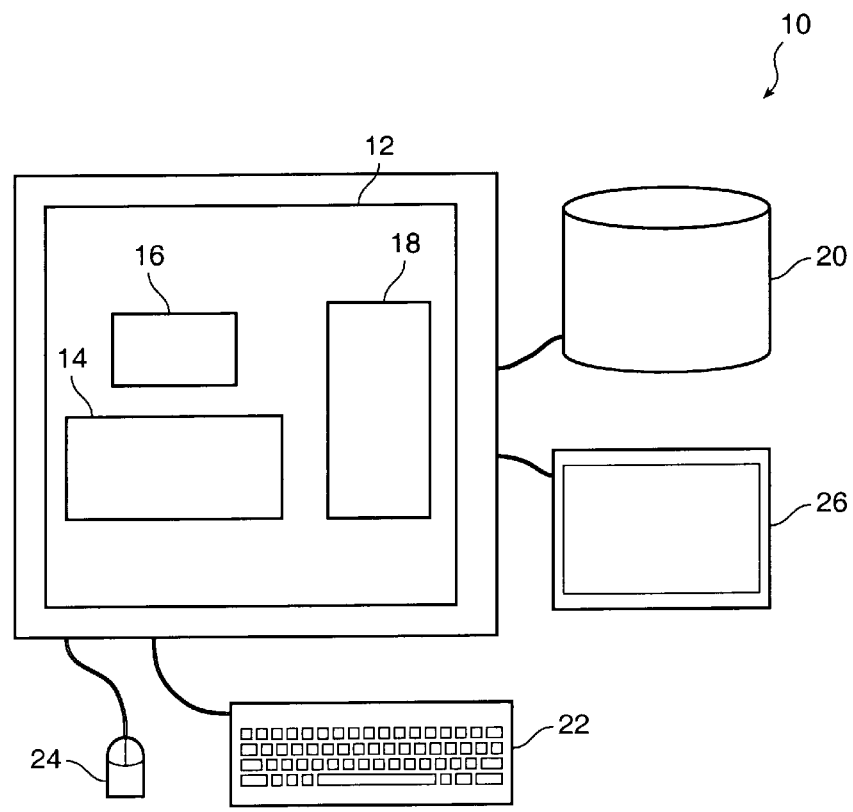
FIG. 1 is a block diagram of a computer system programmed in accordance with a presently preferred embodiment of the present invention.

FIG. 1 is a block diagram of a computer system programmed in accordance with a presently preferred embodiment of the present invention.

A computer system 10 is implemented using an operating system 12 running on a general-purpose processor 14, a medical protocol application program 16, data memory 18, mass storage 20, and input/output devices including a keyboard 22, mouse 24 or other pointing device, and a display monitor 26. Processor 14 is preferably an Intel® Pentium II® processor having an operating speed sufficient to support Windows® NT Server 4.0 as operating system 12. However, in alternative embodiments, other general-purpose processors and compatible operating systems, and other input/output devices would be workable, and are within the scope and spirit of the present invention.

Medical protocol application program 16 is written in the C++ language and may be stored on mass storage 20, or equivalent medium. Data memory 18 is preferably at least 32 megabytes of RAM, while mass storage 20 is preferably of sufficient capacity to hold operating system 12, medical protocol application program 16, and other programs and data files that are needed to support same. Those of ordinary skill in the art will readily recognize that the devices listed immediately above may be substituted with equivalent devices without departing from the inventive concepts disclosed herein and as such, are not intended to limit the present invention in any way. For example, the functional features of the present invention may be written in a language other than C++.

Figure 2:
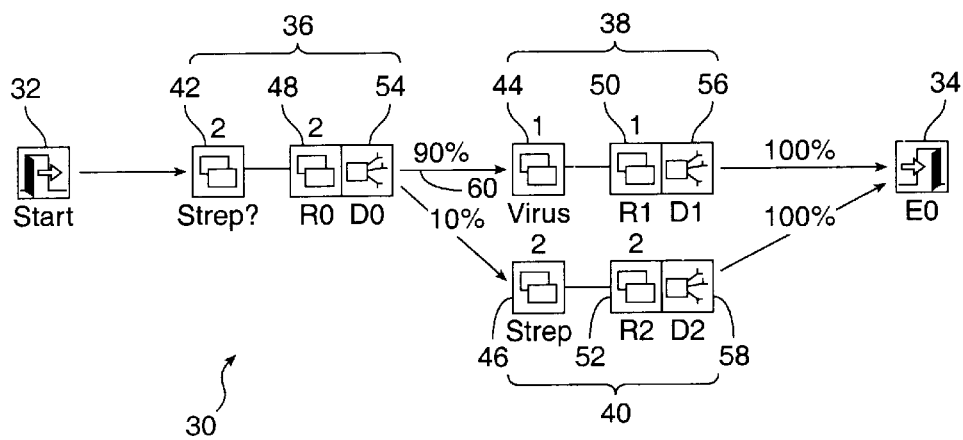
FIG. 2 is an illustration of a template representing a medical protocol in accordance with a presently preferred embodiment of the present invention.

FIG. 2 is an illustration of a template representing a medical protocol in accordance with a presently preferred embodiment of the present invention.

In accordance with a first aspect of the present invention, computer system 10 (FIG. 1) is programmed to display a template 30. Template 30 represents a medical treatment protocol or plan and includes five kinds of graphic elements or building blocks called "nodes." There are five types of nodes: start, order, results, flow control, and exit. Template 30 is showing having a start node 32 which indicates the start of the template, and an exit node 34 which indicates the end of the template. Between start node 32 and exit node 34 are three order triplet icons 36, 38, and 40, each order triplet icon representing an order node 42, 44, and 46, respectively, a result node 48, 50, and 52, respectively, and a flow control node 54, 56, and 58, respectively.

Each of the order triplet icons represents a step within the medical treatment plan and when linked with other nodes, represents a possible step that may be taken in the plan. Each link 60 between two order triplet icons, such as order triplet icon 36 and order triplet icon 38, represents a sequence between two steps within the medical treatment plan. Each sequence, as represented by a link, includes a rule which may be configured by a user of application program 16 to include a time delay. If order triplet icon 36 is configured to have a time delay rule, the process flow of the medical treatment order plan branches to order triplet icon 38 upon the evaluation of the time delayed rule and any other rules that might have been defined for order triplet icon 36. However, order triplet icon 38 is not activated until the time delay expires.

Order nodes contain generalized orders placed during the course of a treatment. Each order node defines a list of generalized orders or healthcare treatment related activities named "order items" that are carried out at a given step in the template. For example, an order node may contain an order to obtain throat cultures from a patient. Order descriptions may be placed into order nodes from a library. Each order is described using attributes that include category, subcategory, name, description, cost, and duration.

A result node shows the status of orders listed in an order node that corresponds to the result node. During patient charting, order results are entered through the result node. Result nodes contain order status (e.g., an order was done or not done) and result values (e.g., electrolyte measurements).

A flow control node contains at least one rule that governs the branching among nodes in the template. Each rule selects a branch at a decision point in a template or plan, and estimates the likelihood of branching down given paths. During patient charting, a flow control node suggests the next step to the health care provider based on the rule(s) and the results entered. The rule(s) may be defined to gather data from a result node that correspond to the same or different order triplet as the current flow control node, from other nodes, or from other template(s), while the results entered are obtained from a result node that correspond to the same order triplet as the flow control node.

When building a template, nodes are positioned in the chronological order in which they are to be carried out or executed. A user defines each node and connects the nodes. Template creation involves the following activities: (1) placing order, results, and flow control nodes in their proper sequence; (2) filling in the orders (i.e., treatment procedures, medicine, and advice); (3) placing an exit node at the end of the template; (4) deciding on the circumstances and order in which each template step is executed during treatment; and (5) saving the template.

Figure 3:
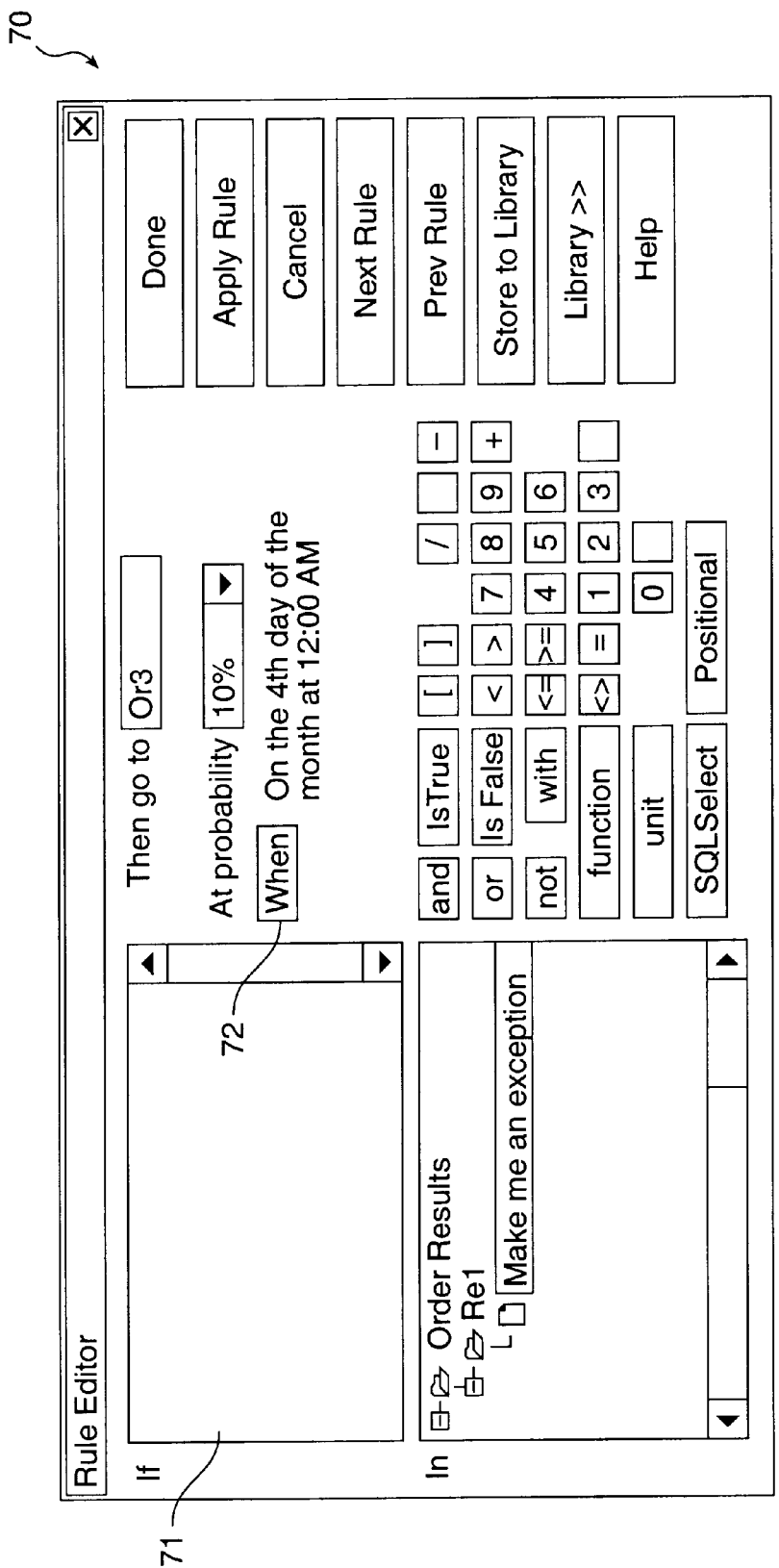
FIG. 3 is an illustration of a rule editor dialog box in accordance with a presently preferred embodiment of the present invention.

FIG. 3 is an illustration of a rule editor dialog box in accordance with a presently preferred embodiment of the present invention.

Rule editor window 70 is launched through an edit rule button in a flow control node window (not shown) corresponding to a selected flow control node. The flow control node is described in the original patent applications and is not further discussed herein to avoid overcomplicating the present disclosure. Rule editor window 70 permits a user to create at least one rule which specifies the conditions under which a branch is to be taken in a selected template. The "If" field 71 provides space for which rules may be created or copied.

Each rule created for a flow control node may be defined as a time delayed rule. In accordance with a presently preferred embodiment of the present invention, two types of time delay rules may be used - relative and absolute.

Figure 4:
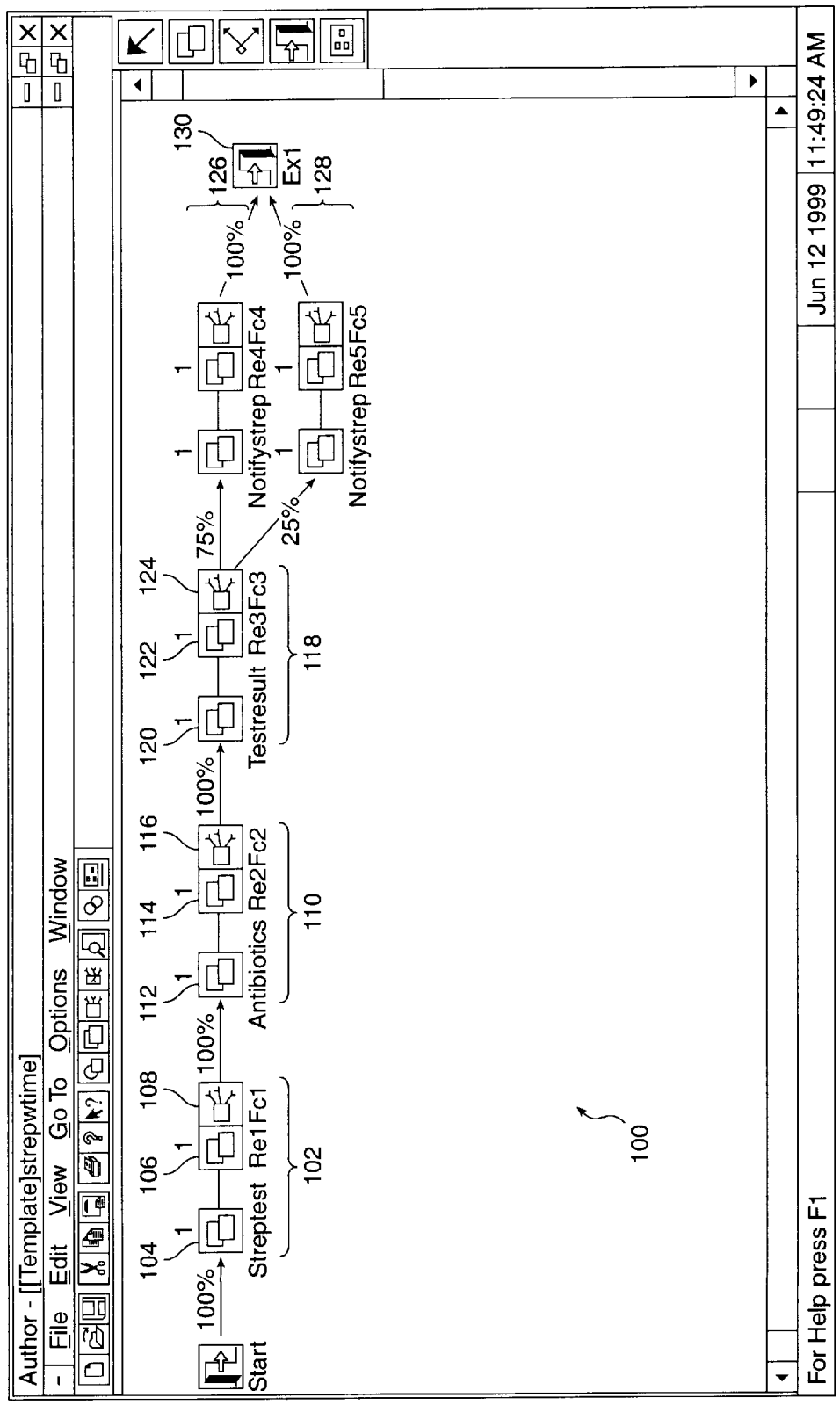
FIG. 4 is an illustration of a time-delay dialog box in accordance with a preferred embodiment of the present invention.

FIG. 4 is a diagram of a template 100 using an order triplet that employs a relative time-delay rule in accordance with a presently preferred embodiment of the present invention.

A relative time delayed rule requires at least two conditions that must be satisfied before the timed delayed rule results in the activation of the next step (as represented by an order triplet or end node in the protocol). The first condition includes the completion of all of the orders listed in the order node which corresponds to the flow control node to which the rule belongs. This condition may be defined by the user or designer of the medical treatment plan template as described in the original patent applications. Thus, a time delayed rule is similar to the rules described in the original patent applications because all of the order conditions specified by the time delayed rule must be satisfied in order to select the next destination or step in the medical protocol.

Requiring that all of the orders be satisfied as a first condition of a relative time delayed rule is not intended to limit the invention in any way. Those of ordinary skill in the art will readily recognize that the first condition may include any number of completed orders. For example, the first condition may include the completion of at least one rather than all of the orders listed in the order node that corresponds to the flow control to which the time delayed rule belongs.

An order is "completed" when the order is entered in the results node which corresponds to the same order triplet to which the relative time delayed rule belongs.

Upon completion of the first condition, a branch to the next step occurs but a second condition (hereinafter referred to as a "time condition") must be satisfied before the next step is activated. Thus, a rule configured with a relative time delay does not automatically result in the activation of the next step (as represented by an order triplet or end node in the protocol). Instead, the next step is not activated until the specified delay period has been reached ("expires").

Branching to the next step after the first condition is satisfied is not intended to limit the present invention in anyway. Those of ordinary skill in the art will readily recognize that branching to the next step may be instead performed when the time condition is satisfied.

For example, referring to FIG. 4, a medical protocol template 100 for treating a possible Strep throat infection is shown. This may protocol may require a first step of administering antibiotics to a patient and a second step for administering another dose of antibiotics in 10 days if the infection has not been completely eradicated. Hence, protocol 100 includes a step 102 which includes an order node 104 having a Strep test order, a results node 106, and a flow control node 108. Flow control node 108 includes a rule which causes the branching and activation of Step 110, if the Strep test results is charted as positive in results node 106.

Step 110 includes an order node 112 which directs the administration of antibiotics, a results node 114, and a flow control node 116. Flow control node 116 includes a relative time delayed rule which causes a branch to step 118 after the administration of the antibiotics is charted in results node 114 (e.g., done, not done) but precludes the activation of step 118 until a specified amount of time has expired, e.g., 10 days, after the charting of the order results in results node 114.

The relative time delayed rule ensures that the next step does not occur immediately after an order is completed (i.e., charted in result node 114). Instead, flow control node 116 evaluates the rule (first condition), branches to the destination node, and starts the delay period (timing condition). Since the rule is defined as a relative time-delayed rule, the destination node, step 118 is not activated until after the delay period expires, which in this example is 10 days.

Upon the expiration of the relative time delay, step 118 is activated. Step 118 includes an order node 120 that has an order for another Strep test to determine whether antibiotics should still be administered. A result node 122 is included for charting the results of the orders listed in order node 120 (e.g., still infected or no longer infected). Flow control 124 node includes a rule which causes a branch to step 126 if the results node 122 includes a still infected result, or a branch to step 128 if the results node 122 includes a no longer infected result.

Upon completion of either step 126 or step 128, medical protocol template branches to exit node 130, completing the medical protocol.

The rule settings, including the relative time delay period defined in flow control node 116, are not shown for each order triplet shown in FIG. 4 but are available by accessing the rule editor window 70 (see FIG. 3) in the flow control node window (not shown) that corresponds to flow control node 116. Alternatively, template 100 may be displayed in a publisher's view, such as that shown in FIG. 9 below.

In accordance with a presently preferred embodiment of the present invention, rule editor window, rule editor window 70 may be launched by highlighting and double-clicking on flow control node 116. This enables a user to determine the settings of flow control node 116, including time delay settings.

Figure 5:
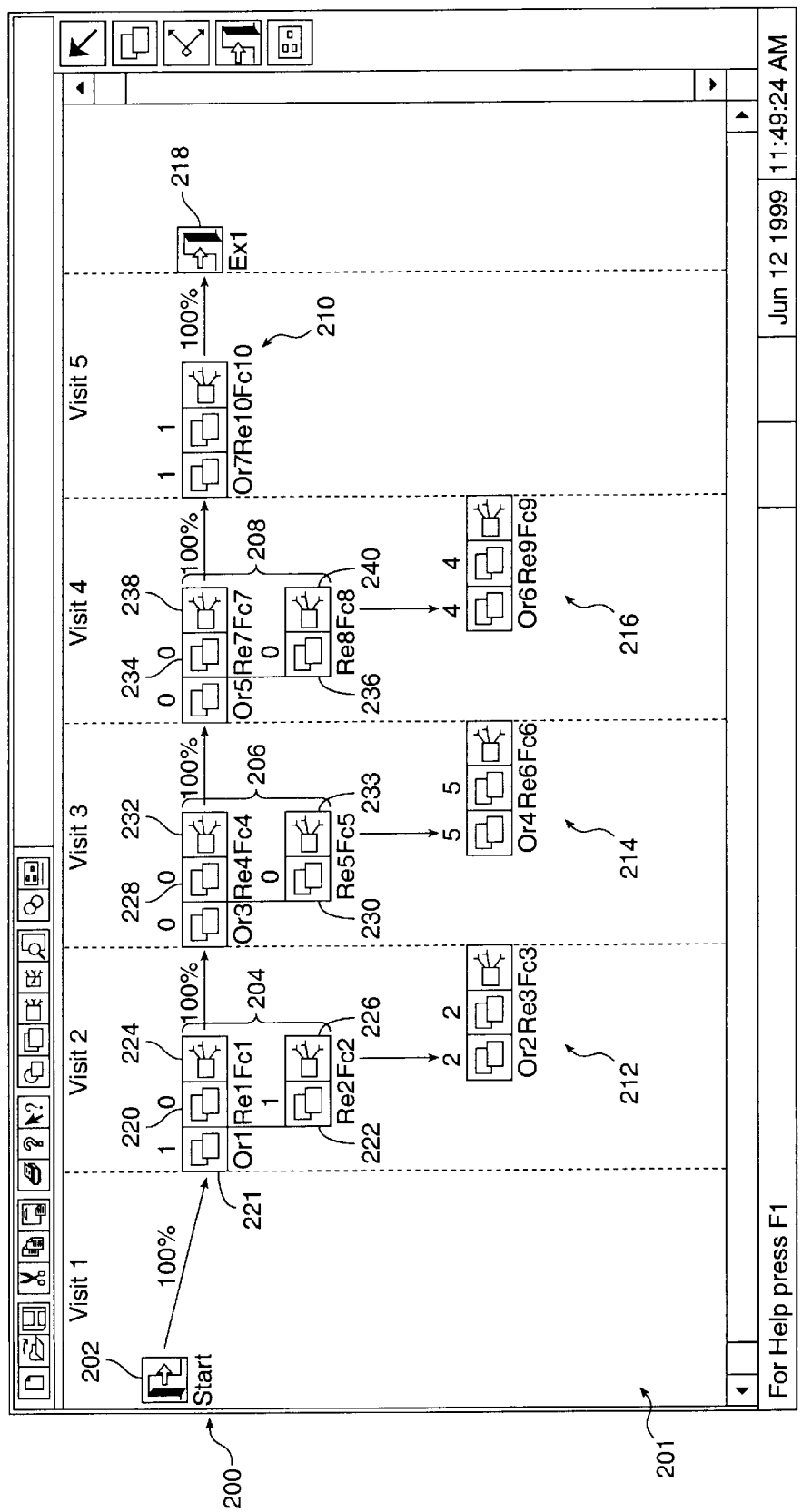
FIG. 5 is a diagram of a template using an order triplet that employs a relative time-delay rule in accordance with a presently prefer-red embodiment of the present invention.

FIG. 5 is an illustration of a parallel path template having order triplets which include absolute time-delay rules in accordance with a presently preferred embodiment of the present invention.

The absolute form of a time delayed rule starts the delay period when its order triplet is activated. It does not depend on the completion of orders to advance the workflow in the template but activates a destination after a specified amount of time has expired. In accordance with a presently preferred embodiment of the present invention, a step requiring an absolute time delayed rule requires parallel paths. A step having a parallel path may be created using the same technique described in U.S. patent application having Ser. No. 08/546,048 and entitled, "AN APPARATUS AND METHOD FOR SPLITTING RESULT NODES IN A GRAPHIC USER INTERFACE," now U.S. Pat. No. 5,786,816, which is incorporated by reference as if fully set forth herein.

When creating the template with parallel paths, the template workflow, which has the absolute time delayed rule, must be executed in a top path 200 while orders are charted in the bottom path(s). This enables a step having an absolute time delayed rule in the workflow to proceed to the next step after the absolute time delay has expired and regardless of whether the order(s) listed in the bottom path of the split node has been completed. Thus, top path 200 does not have any orders.

Parallel path template 201 includes a start node 202; order triplets 204, 206, 208, 210, 212, 214, and 216; and an exit node 218. Order triplet 204 is defined to have two split result nodes, result nodes 220 and 222, and a flow control node 224 defined to have an absolute time delay rule of seven ("7") days (not shown) with a default branch to order triplet 206. Result node 220 is configured to have no expected results (i.e., empty and therefore will automatically provide a workflow that proceeds to flow control node 224. An expected result is defined as a result that corresponds to a listed order within an order node. For example, if order node 221 has an order to provide antibiotics, the expected result for such an order may either be done or not done. Thus, if order node 221 has an order for antibiotics to be administered, result node 220 will be configured not to have an expected result. Thus, the workflow from order node 221 will automatically proceed to flow control node 224.

The rule in flow control node 224 will be then evaluated resulting in a branch to order triplet 206. Since the rule is defined as an absolute time-delayed rule, it will not activate order triplet 206 until the delay period of seven days expires (starting from time the rule is evaluated).

At approximately the same time the workflow proceeds to flow control node 224, result node 222 is also activated because result node 220 is empty. Result node 222 is defined to have one expected result (i.e., it is not empty), which corresponds to the order listed in order node 221, Thus, the workflow for template 201 does not proceed to flow control 226 until the order has been charted as an expected result. Flow control node 226 is defined to have a regular rule (i.e., it is not a time-delay rule), resulting in a branch to order triplet 212 once the order in result node 222 has been charted. Once charted, flow control node 226 branches without delay to order triplet 212, rendering orders within order triplet 212 available for charting.

Order triplet 206 is defined to have two split result nodes, result nodes 228 and 230, and a flow control node 232 defined to have an absolute time-delayed rule of seven ("7") days with a default branch to order triplet 208. Result node 228 is empty and therefore will provide a workflow that automatically proceeds to flow control node 232. The rule in flow control node 232 will be evaluated, resulting in a branch to order triplet 208. Since the rule is defined as an absolute time-delayed rule, it will not activate order triplet 208 until the delay period of seven days expires (starting from time the rule is evaluated).

At approximately the same time the workflow proceeds to flow control node 232, result node 230 is also activated because result node 228 is empty. Result node 230 is defined to have one order (i.e., it is not empty) and hence, its workflow does not proceed to flow control 233 until the order has been charted. Flow control node 233 is defined to have a regular rule which branches to order triplet 214 once the order in result node 230 is charted. Once charted, flow control node 233 branches without delay to order triplet 214, rendering orders within order triplet 214 available for charting.

Order triplet 208 is defined to have two split result nodes, result nodes 234 and 236, and a flow control node 238 defined to have an absolute time-delayed rule of seven ("7") days with a default branch to order triplet 208. Result node 234 is empty and therefore will provide a workflow that automatically proceeds to flow control node 238. The rule in flow control node 238 will be evaluated and result in a branch to order triplet 210. Since the rule is defined as an absolute time-delayed rule, it will not activate order triplet 210 until the delay period of seven days expires.

At approximately the same time the workflow proceeds to flow control node 238, result node 236 is also activated because result node 234 is empty. Result node 236 is defined to have one order (i.e., it is not empty) and hence, its workflow does not proceed to flow control 240 until the order has been charted. Flow control node 240 is defined to have an absolute time-delayed rule, having a delay period of 3 days, which branches to order triplet 216 once the order in result node 236 is charted. Once charted, flow control node 240 branches to order triplet 216 but does not activate it until the delay period of expires 3 days from the time the rule in flow control node has been evaluated.

Order triplets 210 and 216 have regular rules and therefore, require their orders be charted in their respective result nodes before the template workflow can progress to the next destination node. Order triplet 210 will progress to exit node 218 upon charting. Order triplet 216 can end in the manner shown or progress to additional triplets (not shown). Unlike order triplets in the top path, order triplets connected paths below the top path originating from a split node do not have to eventually flow to an exit node.

Note that it may be possible to reach exit node 218 before charting is completed in order triplets 212, 214 and 216. Should this occur, template 200 remains active and will not be archived (or equivalent action) until all orders in template 200 have been charted.

In accordance with a presently preferred embodiment of a first aspect of the present invention, an order triplet may have three functions which facilitate the determination of its status. Each of the functions return either a "true" or "false" status when executed. The first function determines whether a node is active. The second function determines whether a node is done. And the last function determines whether a node has been reached. This will enable application program 16 to allow a rule to check the status of a node in a different plan.

Figure 6:
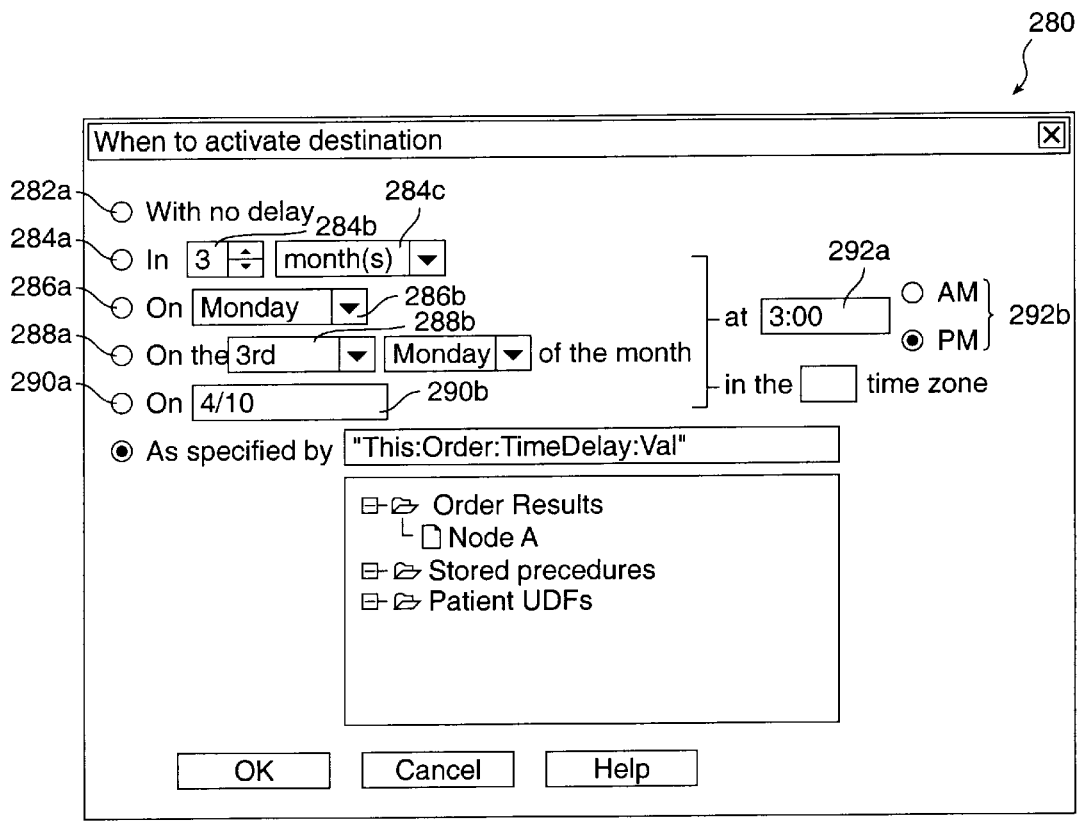
FIG. 6 is an illustration of a parallel path template having order triplets which include absolute time-delay rules in accordance with a presently preferred embodiment of the present invention.

FIG. 6 is an illustration of a time-delay graphical user interface in accordance with a presently preferred embodiment of the present invention.

The delay period for a rule is defined through a delay button 272 (see FIG. 3). When selected, delay button 272 launches a time-delay graphical user interface, such as time delay dialog box 280. In accordance with a preferred embodiment of the first aspect of the present invention, dialog box 280 allows a user to configure a rule to have a time-delay value, such as during the authoring of a template.

The time delay value may be specified in one of several formats using the fields shown in dialog window 280, including a number of units according to a particular scale, a day of the week, a day of the month, or a specific date with an optional year included. The user may also configure the rule to activate a destination node with no time delay by selecting field 282.

If field 284a is selected, the time delay value selected for a rule is configured to have a number of units using number field 284b having a particular scale, such as in minutes, hours, days, weeks, months, or years, using scale field 284c. The format of the time delay must be within a set having values that include: minutes, hours, days, weeks, months or years. Selecting field 284a starts the rule's delay period upon the activation of the order triplet for which the rule corresponds. This type of delay period creates an absolute time delay. Absolute time delay rules are further described below.

If field 286a is selected, the time delay value is configured to have a delay period according to a day of the week (i.e., Monday, Tuesday, Wednesday, Thursday, Friday, Saturday, or Sunday) using field 286b. The destination node is then activated when that day of the week arrives.

If field 288a is selected, the time delay value is configured to have a delay period according to a selected day within any given month (such as the 1st day of the month, the 2nd day of the month, etc., . . .) using field 288b. The destination node is then activated when that day of the month arrives.

If field 290a is selected, the time delay value is configured to have a delay period according to a selected day and month for any given year using field 290b. Alternatively, the user may also select the year. Specifically, the format includes having a time delay which is entered in a month and day format (i.e., mm/dd) or a month, day, and year format (i.e., mm/dd/yy). The destination node is then activated when the date specified arrives.

For any of the date formats described above, the user may also select a specific time by using fields 292a and 292b. For example, the user may enter a time of 3 PM by entering the number "3" in field 292a and selecting the "PM" designation in field 292b.

Alternatively, the present invention may be programmed to receive the time delay from a form field, a UDF (user defined field) or a stored procedure, where the entered time delay must match a syntax that corresponds to any one of the following forms.

All of the formats may optionally be followed by hours and minutes followed by a morning (AM) or evening designation (PM).

In accordance with a presently preferred embodiment of the present invention, the type of time delay, i.e., relative or absolute, defined by the time-delay value is dependent on whether the result node corresponding to the flow control node having the time-delay has been configured with at least one expect result (i.e., the result node is not empty). If the result node is not empty, such as order node 112 in FIG. 4, then the rule is treated by the present invention as a relative time-delay rule.

However, a time delay value corresponding to a flow control node following a split result node which is empty, such as split result node 220 within top path 200 in FIG. 5, is used by the present invention as the delay period for an absolute time-delay rule. As described above, an empty split result node by definition does not include expected results.

Figure 7:
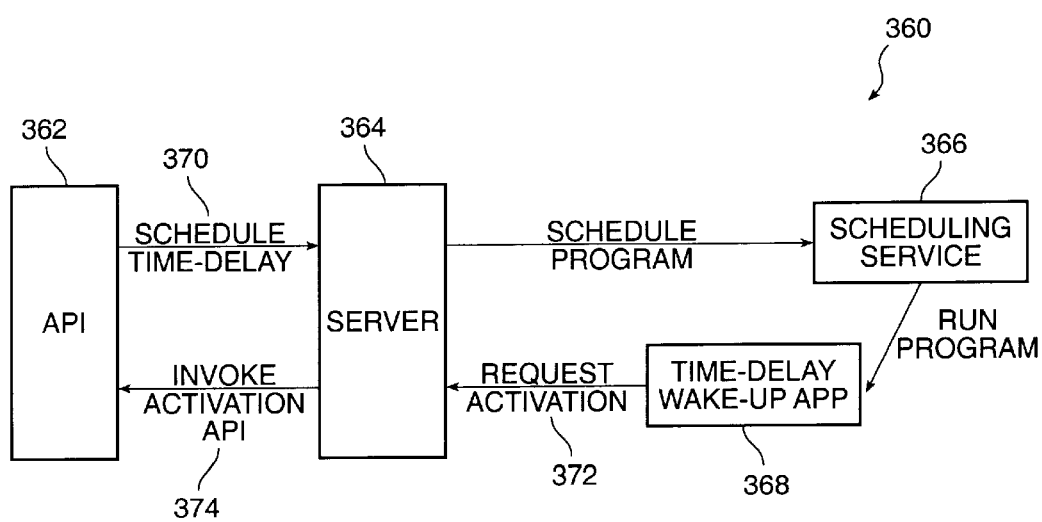
FIG. 7 is a block diagram of a software architecture for providing time delay information in a medical protocol system programmed to operate on a computer system in accordance with a presently preferred embodiment of the present invention.

FIG. 7 is a block diagram of a software architecture for providing time delay information in a medical protocol system programmed to operate on a computer system in accordance with a presently preferred embodiment of the present invention.

Software architecture 360 shows an application programming interface 362 (API), a server 364, a scheduling program 366, and a time-delay wake-up application 368. In accordance with a presently preferred embodiment of the first aspect of the present invention, application programming interface 362 is intended to provide interface functions between application program 16 (FIG. 1) and workflow server 364. Workflow server 364 preferably is configured to have the Windows™ NT Server 4.0 operating system and uses the NT scheduling service provided by the operating system as scheduling program 366. This configuration is not intended to be limiting in any way. Those of ordinary skill in the art will readily recognize that other operating systems that provide similar features to Windows® Server 4.0 and scheduling program 366 may also be used.

When a time-delay rule is evaluated and met ("fired"), API 362 resolves the time delay information received from the time delay dialog window into a date and time in which the delay information is to expire. For example, if the time delay information pertains to a relative time-delay rule, then the delay period will start from the time the rule is evaluated and met. API 362 also provides a time-delay function call 370, which schedules the date and time, to server 364. Server 364 responds by scheduling a wake-up function 368 with scheduling service 366. This enables server 364 to run wake-up function-368 when the date and time is met (i.e., when the delay information expires). Wake up function 368 generates a request 372, resulting in server 364 generating an activation request 374. API 362 receives the activation request 374 and processes it by activating the destination node.

Figure 8:
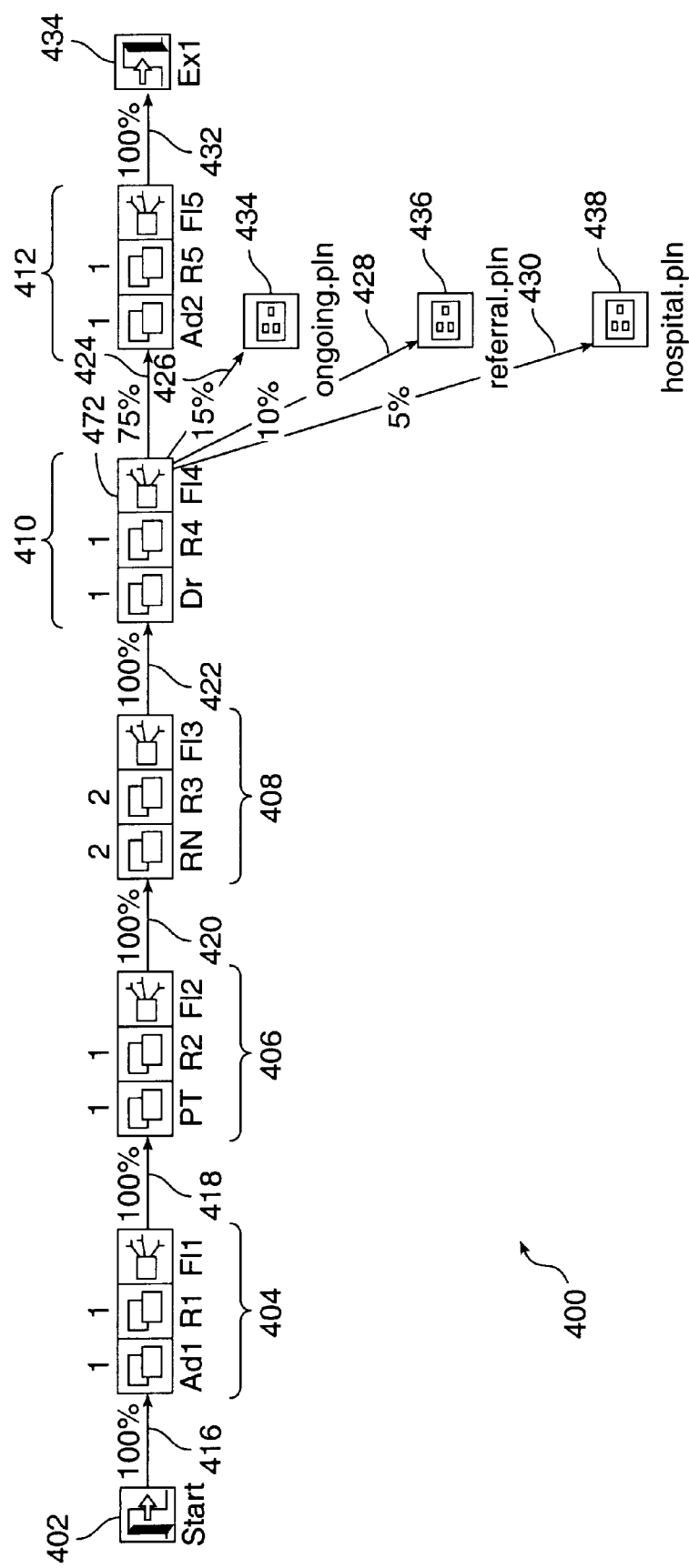
FIG. 8 is an illustration of a template having a set of order triplets which define the steps within a medical protocol in accordance with a preferred embodiment of the present invention.

FIG. 8 is a diagram of a template having a set of order triplets which define the steps within a medical protocol in accordance with a preferred embodiment of the present invention.

Template 400 includes a start node 402 and order triplets 404, 406, 408, 410, and 412 and exit node 414 and reflects a medical protocol for a typical ambulatory care visit which is to be performed by a medical practitioner. The nodes are coupled through flow control connections 416, 418, 420, 422, 424, 426, 428, 430, and 432 as shown in FIG. 6. Each of the flow control connections are associated with percentages reflecting the probability of occurrence for a connected node so that a cost estimate may be generated for template 400. This cost feature is described in the original patent applications and will not be further discussed to avoid overcomplicating the within disclosure. The percentages do not in any way affect the branching decisions made between each node.

Order triplet 410 is shown having a flow control node that may branch to three possible templates or plans. Template 434 represents a medical process pertaining to an ongoing plan, such as a plan for processing a current patient. Template 436 represents a medical process pertaining to a referral plan, such as a plan for referring a patient to a specialist. And template 438 represents a medical process pertaining to a hospitalization plan, such as a plan for preparing a patient for hospitalization. The number of templates, the number of templates, or branches, etc., shown is not intended to limit the invention in any way. Those of ordinary skill in the art will recognize that a template having any possible configuration may be created using the five nodes and the graphical user interfaces described herein and in the original patent applications.

Figure 9:
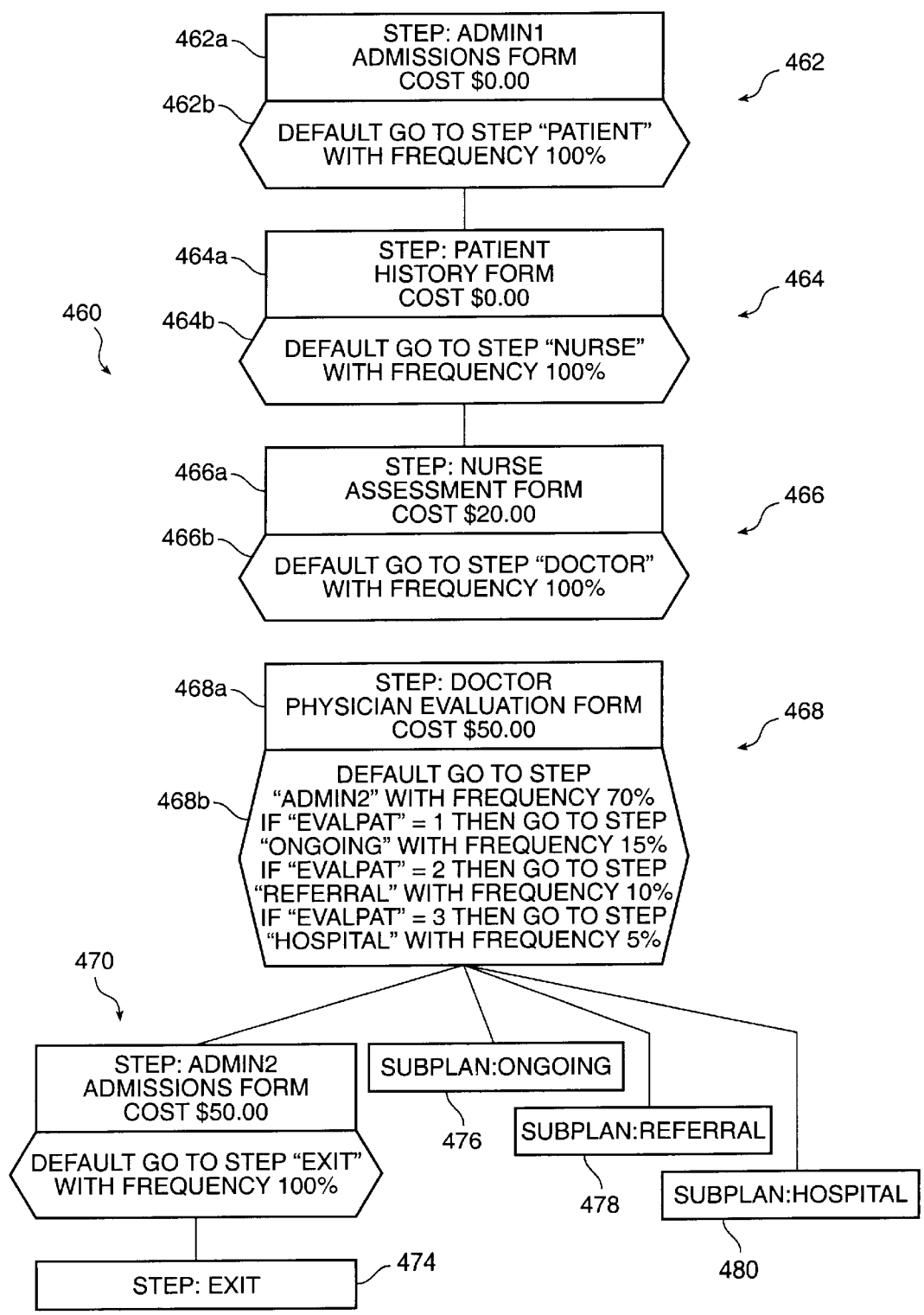
FIG. 9 is an illustration of a publisher's view of the template shown in FIG. 8 in accordance with an alternative embodiment of the present invention.

FIG. 9 is a publisher's view of the template shown in FIG. 8 in accordance with an alternative embodiment of the present invention.

According to a second aspect of the present invention, publisher's view 460 permits a user of application program 16 to see the contents of a process flow, such as orders and rules, defined for each order triplet within a template, such as template 400, and the possible flows in which the order triplets may be activated or performed. Preferably the steps in the process flow are arranged in a top down manner. Each step is shown with a rectangular and six-sided blocks with each square block containing the details of the orders contained in the step and the six-sided shaped block containing the rule(s) associated with the step. The shapes of the blocks used to show the contents of the orders and the rules associated with a step are not intended to limit the invention in any way. Those of ordinary skill in the art will readily recognize that other types of shaped blocks may be used and are within the scope and spirit of the present invention.

As show in in FIG. 9 steps 462, 464, 466, 468, and 470 correspond to the orders, results, and flow connection described in order triplets 404, 404, 406, 408, 410, and 412. Step 462 displays the contents of order triplet 404 which include an admissions form order and a default rule which results in a branch to step 464. The admissions form order and the default rule are shown in rectangular and six-sided blocks 462*a* and 462*b*, respectively.

Step 464 displays the contents of order triplet 406 which include a history form order and a default rule which branches to step 466. The history form order and the default rule are shown in rectangular and six-sided blocks 464*a* and 464*b* respectively.

Step 466 displays the contents of order triplet 408, including an assessment form order and a default rule which branches to step 468. The assessment form order and the default rule are shown in rectangular and six-sided blocks 466*a* and 466*b*, respectively. A cost of $20.00 is associated with the order but, as described above, is not considered by application program 16 when interpreting the rules in the template.

Step 468 is similar to steps 462, 464, and 466 because it displays the contents of order triplet 410, including a physician evaluation form order. But unlike the other steps it has rules which result in one of four possible branches. The physician evaluation form order and the rules are shown in rectangular and six-sided blocks 468*a* and 468*b*, respectively. The first rule branches to step 470 if the other rules in flow control node 472 (FIG. 8) are not met.

Step 470 displays the contents of order triplet 412, including a final visit form step and a default rule that branches to step 474. Step 474 displays the contents of end node 414.

Returning to step 468, a second rule checks whether the variable, such as "EvalPerf", is equal to "1," or other selected value, and if so flow control node 472 activates step 476 which corresponds to template 434. Similarly, a third rule checks whether the variable, such as "EvalPerf", is equal to "2," or other selected value, and if so flow control node 472 activates step 478 which corresponds to template 436. A fourth rule checks whether the variable, such as "EvalPerf", is equal to "3," or other selected value, and if so flow control node 472 activates step 480 which corresponds to template 438.

While embodiments and applications of this invention have been shown and described, it would be apparent to those skilled in the art that many more modifications than mentioned above are possible without departing from the inventive concepts and scope herein. The invention, therefore, is not to be restricted except in the spirit of the appended claims.

We claim:

1. A method for displaying a graphic representation of a medical treatment plan using a computer system, the method comprising the steps of:

providing a plurality of order triplets, each of said order triplets representing a step within the medical treatment plan;

representing a sequence within the medical treatment plan by linking graphically a first order triplet and a second order triplet, said first and second order triplets from said plurality of order triplets;

associating a rule with said sequence;

associating a time delay with said rule; and activating said second order triplet upon expiration of said time delay.

2. The method of claim 1, wherein said step of linking includes using a process flow connection.

3. The method of claim 1, wherein said step of associating a time delay includes a step of starting said time delay when said order triplet from said plurality of order triplets is activated.

4. The method of claim 1, wherein said step of associating a time delay includes a step of starting said delay period when said first order triplet is activated.

5. The method of claim 1, wherein said set of requirements further includes completion of a step represented by said first order triplet.

6. The method of claim 1, further including a step of providing a start node, said start node for indicating a starting order triplet icon within the medical treatment plan.

7. The method of claim 1, further including a step of providing an end node, said end node for indicating an ending step within the medical treatment plan.

8. The method of claim 1, further including a step of providing an order node, a result node, and a flow control node to comprise each of said order triplets.

9. The method of claim 8, further including a step of representing through said order node at least one healthcare treatment related activity that is to be carried out by a healthcare provider when said order triplet is activated.

10. The method of claim 8, further including a step of representing a result of said healthcare treatment related activity through said result node.

11. The method of claim 8, further including a step of providing at least one rule through said flow control node, said rule for governing branching between said order triplets.

12. The method of claim 8, further including the steps of:

representing through said order node at least one healthcare treatment-related activity that is to be carried out by a healthcare provider when said order triplet is activated;

representing at least one result of said healthcare treatment-related activity through said result node; and providing at least one rule in said flow control node, said at least one rule for governing branching between said order triplets.

13. The method of claim 12, further including a step of providing a publisher view by representing said sequence within the medical treatment plan as a flow chart by using said at least one healthcare treatment-related activity and said at least one result to define said flow chart.

14. A method for displaying a graphic representation of a medical treatment plan using a computer system, the method comprising the steps of:

providing a plurality of order triplets, each of said order triplets representing a step within the medical treatment plan;

representing a sequence within the medical treatment plan by using a process flow connection to link graphically a first order triplet and a second order triplet, said first and second order triplets from said plurality of order triplets;

associating a rule with said sequence, said rule having at least one condition;

associating a time delay with said rule; and activating said second order triplet upon satisfaction of a set of requirements, said set of requirements including satisfaction of said condition and expiration of said time delay.

15. The method of claim 14, wherein said step of associating a time delay includes a step of starting said time delay when a beginning order triplet from said plurality of order triplets is activated.

16. The method of claim 14, wherein said step of associating a time delay includes a step of starting said delay period when said first order triplet is activated.

17. The method of claim 14, wherein said set of requirements further includes completion of a step represented by said first order triplet.

18. A method for displaying a graphic representation of a medical treatment plan using a computer system, the method comprising the steps of:

providing a first order triplet having a first order triplet, a first result node is having at least one result value, and a first flow control node having a time delay rule, said first order triplet representing a first step within the medical treatment plan;

providing a second order triplet having a second order triplet, a second result node, and a second flow control node, said second order triplet representing a second step within the medical treatment plan;

representing a sequence within the medical treatment plan by linking graphically said first order triplet and said second order triplet; and associating a rule with said sequence, said rule having at least one condition;

associating a time delay with said rule; and activating said second order triplet upon satisfaction of a set of requirements, said set of requirements including satisfaction of said condition and expiration of said time delay.

19. The method of claim 18, wherein said step of linking includes using a process flow connection.

20. The method of claim 18, wherein said step of associating a time delay includes a step of starting said time delay when a beginning order triplet from said plurality of order triplets is activated.

21. The method of claim 18, wherein said step of associating a time delay includes a step of starting said delay period when said first order triplet is activated.

22. The method of claim 18, wherein said set of requirements further includes completion of a step represented by said first order triplet.

23. An apparatus for displaying a graphic representation of a medical treatment plan, the apparatus comprising:

means for providing a plurality of order triplets, each of said order triplets representing a step within the medical treatment plan;

means for representing a sequence within the medical treatment plan by linking graphically a first order triplet and a second order triplet, said first and second order triplets from said plurality of order triplets;

means for associating a rule with said sequence, said rule having at least one condition;

means for associating a time delay with said rule; and activating said second order triplet upon satisfaction of a set of requirements, said set of requirements including satisfaction of said condition and expiration of said time delay.

24. The apparatus of claim 23, wherein said means for linking includes using a process flow connection.

25. The apparatus of claim 23, wherein said means for associating a time delay includes a step of starting said time delay when a beginning order triplet from said plurality of order triplets is activated.

26. The method of claim 23, wherein said means for associating a time delay includes a step of starting said delay period when said first order triplet is activated.

27. The method of claim 23, wherein said set of requirements further includes completion of a step represented by said first order triplet.

28. A data processing apparatus, comprising:

a display for displaying data;

input means for supplying input data;

a storage location, coupled with the display and the input means, for storing data, images, and programs; and processing means, coupled to the display means, the input means, and the storage means, for controlling the storage means, the input means, and the display means in response to stored programs and input data to perform data processing operations;

wherein the display includes:

a plurality of order triplet icons stored in said storage location, each of said order triplets representing a step within the medical treatment plan;

a sequence within the medical treatment plan having a first order triplet icon linked graphically with a second order triplet icon, said first and second order triplet icons from said plurality of order triplet icons;

a rule with said sequence, said rule having at least one condition and responsive to a time delay; and a second order triplet activated upon satisfaction of a set of requirements, said set of requirements including satisfaction of said condition and expiration of said time delay.

29. The apparatus of claim 28, further including a process flow connection having said rule, said process flow connection for graphically linking said first order triplet icon and said second order triplet icon.

30. The apparatus of claim 28, wherein said time delay includes a step of starting said time delay when a beginning order triplet icon from said plurality of order triplet icons is activated.

31. The method of claim 28, wherein said time delay includes a step of starting said delay period when said first order triplet icon is activated.

32. The method of claim 28, wherein said set of requirements further includes completion of a step represented by said first order triplet.

33. An apparatus comprising:

a general-purpose computer having:

means for providing a plurality of order triplets, each of said order triplets representing a step within the medical treatment plan;

means for representing a sequence within the medical treatment plan by linking graphically a first order triplet and a second order triplet, said first and second order triplets from said plurality of order triplets;

means for associating a rule with said sequence, said rule having at least one condition;

means for associating a time delay with said rule; and means for activating said second order triplet upon satisfaction of a set of requirements, said set of requirements including satisfaction of said condition and expiration of said time delay.

34. The apparatus of claim 33, wherein said means for linking includes using a process flow connection.

35. The apparatus of claim 33, wherein said means for associating a time delay includes a step of starting said time delay when a beginning order triplet from said plurality of order triplets is activated.

36. The of claim 33, wherein said means for associating a time delay includes a step of starting said delay period when said first order triplet is activated.

37. The of claim 33, wherein said set of requirements further includes completion of a step represented by said first order triplet.

* * * * *